(12) United States Patent
Woodward

(10) Patent No.: US 8,985,057 B2
(45) Date of Patent: Mar. 24, 2015

(54) SYSTEM FOR DEVELOPMENT OF THERAPEUTIC DRUGS AND PROCEDURES

(76) Inventor: Donald J. Woodward, Winston Salem, NC (US)

(*) Notice: Subject to any disclaimer, the term of this patent is extended or adjusted under 35 U.S.C. 154(b) by 42 days.

(21) Appl. No.: 13/593,802

(22) Filed: Aug. 24, 2012

(65) Prior Publication Data

US 2014/0058214 A1    Feb. 27, 2014

(51) Int. Cl.
*A01K 1/03* (2006.01)
*A61B 5/11* (2006.01)
*A61B 5/155* (2006.01)
*A61B 5/00* (2006.01)
*A61D 3/00* (2006.01)
*A61B 5/04* (2006.01)
*A61B 5/15* (2006.01)

(52) U.S. Cl.
CPC ............. *A01K 1/031* (2013.01); *A61B 5/04001* (2013.01); *A61B 5/1126* (2013.01); *A61B 5/1427* (2013.01); *A61B 5/15003* (2013.01); *A61B 5/150992* (2013.01); *A61B 5/155* (2013.01); *A61B 5/4848* (2013.01); *A61B 2503/40* (2013.01); *A61D 3/00* (2013.01)
USPC ........................................................ 119/421

(58) Field of Classification Search
CPC ........................................................ A01K 1/03
USPC .................. 119/416, 417, 421; 128/897, 898; 340/573.1, 573.3; 248/58, 60, 61, 63
See application file for complete search history.

(56) References Cited

U.S. PATENT DOCUMENTS

| | | | | |
|---|---|---|---|---|
| 2,122,988 | A | * | 7/1938 | Nelson .......................... 378/194 |
| 3,897,751 | A | * | 8/1975 | Gullino et al. ................ 119/420 |
| 5,816,256 | A | * | 10/1998 | Kissinger et al. ............. 128/897 |
| 5,832,878 | A | * | 11/1998 | Bonsall et al. ................ 119/769 |
| 6,161,045 | A | | 12/2000 | Fischell et al. |
| 6,279,511 | B1 | * | 8/2001 | Loughnane ................... 119/769 |
| 6,366,813 | B1 | | 4/2002 | DiLorenzo |
| 6,993,392 | B2 | | 1/2006 | Nicolelis et al. |
| 7,258,672 | B2 | * | 8/2007 | Hansson et al. .............. 600/581 |
| 7,665,424 | B2 | * | 2/2010 | Denault et al. ................ 119/792 |
| 2006/0116738 | A1 | | 6/2006 | Wolf et al. |
| 2007/0239059 | A1 | | 10/2007 | McIver |
| 2007/0249955 | A1 | | 10/2007 | Carlson et al. |
| 2007/0250133 | A1 | | 10/2007 | Carlson et al. |
| 2013/0255586 | A1 | * | 10/2013 | Gerashchenko .............. 119/421 |

OTHER PUBLICATIONS

PIC Microcontrollers, Wikipedia article <"http://en.wikipedia.org/wiki/PIC_microcontroller">, Sep. 2, 2014.

* cited by examiner

*Primary Examiner* — Rob Swiatek
*Assistant Examiner* — Ebony Evans
(74) *Attorney, Agent, or Firm* — James G. Passé; Passé Intellectual Property, LLC

(57) ABSTRACT

A device and method for delivering drugs or sending or receiving information to or from a lab test animal over a long period of time without having the cords attached to the animal tangle as it moves around in its enclosure.

28 Claims, 5 Drawing Sheets

SYSTEM FOR DEVELOPMENT OF THERAPEUTIC DRUGS AND PROCEDURES

COPYRIGHT NOTICE

A portion of the disclosure of this patent contains material that is subject to copyright protection. The copyright owner has no objection to the reproduction by anyone of the patent document or the patent disclosure as it appears in the Patent and Trademark Office patent files or records, but otherwise reserves all copyright rights whatsoever.

BACKGROUND OF THE INVENTION

1. Field of the Invention

The present invention relates to a method or system of performing experiments and testing therapeutic drugs and experimental procedures on a test animal. In particular, the present invention relates to a system for delivering optical, fluid, and electrical neuronal data to and from a test animal and/or applying one or more procedures to the animal at the same time while compensating for animal movement to prevent, over long times, twisting of the cable connections for fluid exchange and sampling, optical or electrical connections. The system is designed for chronic application and implantation within an animal model (including human) test subject. The system also defines a process and system for creating therapies.

2. Description of Related Art

Multichannel microwire arrays, carbon fibers, microfabricated silicon or ceramic electrode arrays for acquiring neural signals and chemical signals from large numbers of single neurons and from multiple brain or body regions, and for stimulation of brain regions, are known in the art. Arrays usually comprise one or more microwires, multisite probes with specialized chemical sensor sites, or carbon electrodes. One or more connectors, flexible cable connectors with leads, or printed circuit boards are in electrical connection with the electrodes. These connectors are useful for studying higher order functions of the brain and actions of drugs in relation to behavior during stimuli which cannot be determined with single or small numbers of neuronal connections. The brain and body consists of a complex biological system that requires concurrent observation and causal probing at many interconnected sites to reveal function and to develop therapeutic strategies.

While this type of interface is capable of measuring very specific activity of the brain during stimulation or behavioral constraints with a great deal of information being acquired or delivered, the ability to do so with a moving animal subject, such as a mouse or rat has been limited. Originally, the most common method of dealing with an awake animal during measurements was to restrain the subject to prevent them from disturbing contacts of probes with neurons, twisting the connections, and thus, damaging the connections, the animal, or both. This makes long term studies very difficult to conduct and studies where the animal must move to create the stimulus is impossible. This is true for all animal connections including optical, fluid, and electrical connections.

The problem of allowing the animal to move freely while maintaining multiple electrical including video, fluid, or optical connections is exacerbated by the need for a rotating swivel for each type of connection. Frequently, in the past, the problems with the addition of multiple connections to animals during testing was dealt with by use of slip ring bushings which allowed the connecting lines to the high density array each to twist, thus, preventing twisted lines. However, for multiple animals, and in general, the slip rings are expensive to use and to coordinate, may introduce electrical noise, and therefore are a problem of their own.

A similar problem applies to connections needed to control electrical stimulation in multiple areas such as the brain. Also difficult for these reasons is the use of multiple sensors that require a combination of electrical stimulation and recording. Sensors of many types have this common difficulty. These may include combinations of functions for electrical recording, electrical stimulation, chemical sensing, pressure detectors, movement and mechanical deformation sensors, optical stimulation, optical sensing, video capture, sound sensing in the auditory range, ultrasound for imaging, stimulation, and fluid flow measurement. It is clear that the difficulties to be addressed are common to multiple sensor/stimulation systems that need to operate in parallel and that require connections to external instrumentation. Typically, the larger the numbers of connections and type, the more difficulties arise.

Chronic dosing of an animal or sampling of body fluids by attachment of multiple fluid drug sources with a control to regulate the timing and amount of a delivered drug or obtaining a fluid sample is an even greater problem. A rotatable fluid swivel connector is not a very effective means of delivering multiple types of fluid drug doses. They are cumbersome and it is difficult to prevent leaks with multiple fluid connections. Accordingly, the combination of delivering drugs and simultaneously performing multichannel array neuronal readings has been almost impossible to accurately and consistently accomplish over the periods of time necessary to perform drug testing on animals with parallel behavioral assessment. Even further, research with this type of measurement is limited at best and data is not useful enough to be consistently accurate. Use of lasers to apply light stimulation to multiple sites, and light sensors, scanners or imagers are also burdened with this problem.

Of great use would be a system that allows for administration of therapeutic test drugs and other experimental manipulations while monitoring or stimulating neuronal activity and behavior through multiple modes involving fluids optically or electrically connecting to a moving animal that can easily be accomplished during tests over long periods of time, and especially for simultaneous use with multiple animals to achieve high throughput testing for development of therapies.

BRIEF SUMMARY OF THE INVENTION

The present invention relates to an animal testing system wherein the experimental and therapeutic liquid sources, electrical connections for stimulation, optical stimulation and recording, and the circuit board controlling flow of information from the connections are mounted on a rotating platform positioned over an animal chamber, thus, allowing the circuit board, fluid containers, and other devices to be rotated with the animal rather than the connections being rotated. The rotation is accomplished by use of movement detectors which input animal movement to a circuit board, and thus can cause the platform to be rotated in coordination with the animal movements. Tangling and other problems of this type of testing are avoided and long term animal studies can be accomplished with this system. Small electronic parts and computer processor boards are utilized so that inertia can be overcome and so that all operating parts can rotate with the animal.

Accordingly, in one embodiment of the present invention, there is disclosed an animal test system for use with a moving tethered test animal comprising:

a. an animal chamber having a bottom surface for containing the test animal;

b. a rotating platform positioned above the animal chamber bottom;

c. a motor for rotating the platform clockwise or counterclockwise;

d. at least one connector for a tethered connection to the animal for delivering or receiving at least one of optical, electrical, or fluid connection to the animal wherein an opposite end of the connection is positioned on the platform;

e. one or more movement sensors positioned near the connector or in the chamber to sense the movement of the animal in the chamber wherein the sensors are used to send movement data to a digital feedback system which controls the motor to rotate the platform clockwise or counterclockwise based on the animal movement sensed in a manner to prevent unwanted twisting of the animal tethered connection; and f. a digital data system in digital communication with the connection to the animal.

Yet another embodiment comprises a method for testing a drug in one or more animals positioned in an animal chamber comprising:

a. positioning a motorized rotating platform above a floor of the chamber;

b. placing a desired quantity of the drug in liquid form in a drug delivery container, positioning the container on the platform, and creating a tethered connection of the drug container to the animal;

c. positioning one or more movement sensors to sense the movement of the animal in the chamber which can control a motor to rotate the platform clockwise or counterclockwise based on the animal movement sensed in a manner to prevent unwanted twisting of the animal connection to the drug container;

d. delivering the drug to the animal;

e. optionally sampling fluids from the animal's brain or body in a desired manner; and f. monitoring the results of the administered drug while rotating the platform to account for the animal movement.

An important feature of one embodiment is that data collection from the animal is done by a computer, with disk storage or other digital collection system that also rotates with the animal though it could be remote or particularly on the system and particularly of the system. The collection system and all other devices receive power through a set of slip rings. Data are transmitted from the rotating unit by one or more means including wireless transmission, optical rotating commutators, or the like. Time synchronizing pulses are connected to the digital collection system via a slip ring, high speed wireless, optical links, or the like.

DETAILED DESCRIPTION OF THE INVENTION

Figure 1:
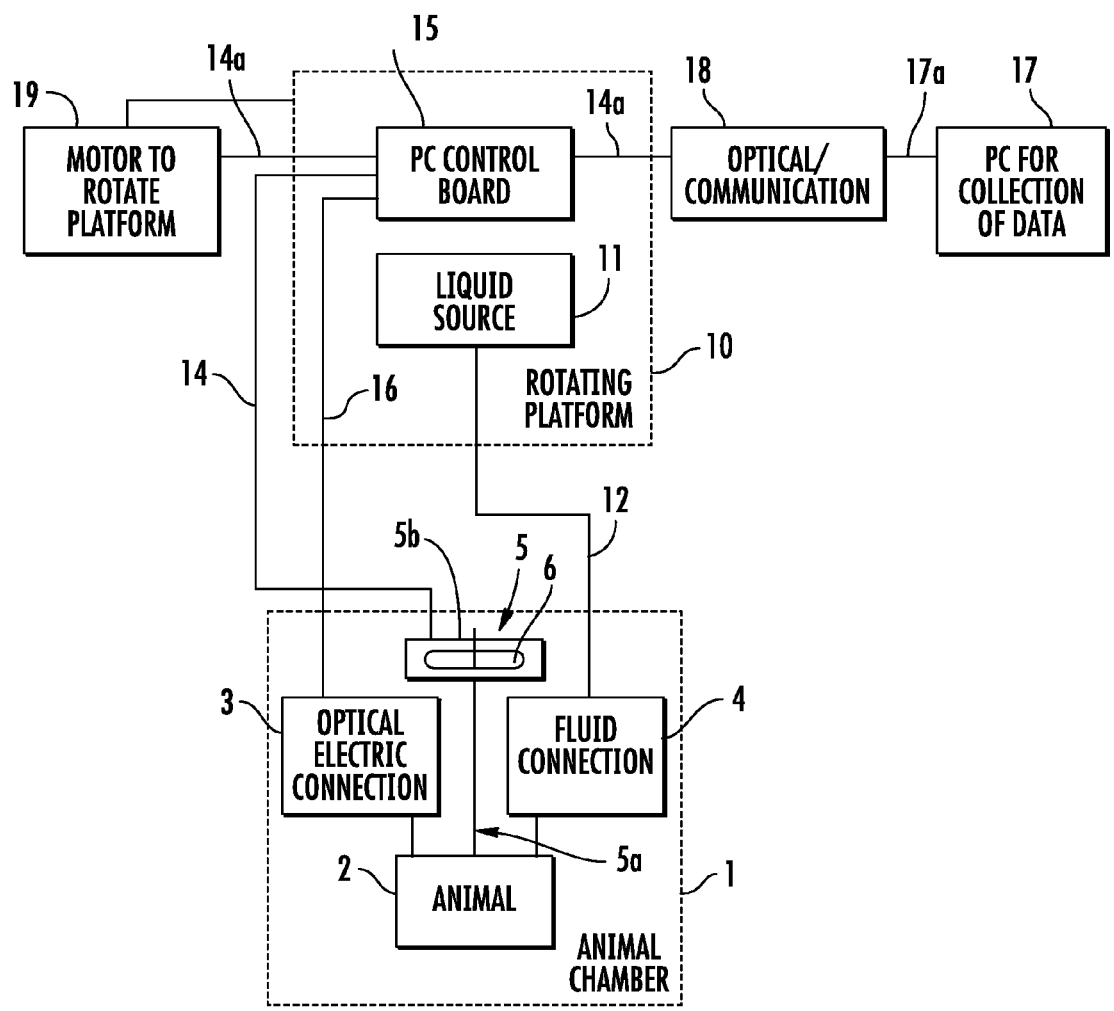
FIG. 1 is a relationship chart of an embodiment of the present invention.

While this invention is susceptible to embodiment in many different forms, there is shown in the drawings and will herein be described in detail specific embodiments, with the understanding that the present disclosure of such embodiments is to be considered as an example of the principles and not intended to limit the invention to the specific embodiments shown and described. In the description below, like reference numerals are used to describe the same, similar or corresponding parts in the several views of the drawings. This detailed description defines the meaning of the terms used herein and specifically describes embodiments in order for those skilled in the art to practice the invention.

DEFINITIONS

The term "about" means ±10 percent.

The term "essentially" means ±10 percent.

The term "comprising" is not intended to limit inventions to only claiming the present invention with such comprising language. Any invention using the term comprising could be separated into one or more claims using "consisting" or "consisting of" claim language and is so intended.

The terms "a" or "an", as used herein, are defined as one or as more than one. The term "plurality", as used herein, is defined as two or as more than two. The term "another", as used herein, is defined as at least a second or more. The terms "including" and/or "having", as used herein, are defined as comprising (i.e., open language). The term "coupled", as used herein, is defined as connected, although not necessarily directly, and not necessarily mechanically.

Reference throughout this document to "one embodiment", "certain embodiments", and "an embodiment" or similar terms means that a particular feature, structure, or characteristic described in connection with the embodiment is included in at least one embodiment of the present invention. Thus, the appearances of such phrases or in various places throughout this specification are not necessarily all referring to the same embodiment. Furthermore, the particular features, structures, or characteristics may be combined in any suitable manner in one or more embodiments without limitation.

The term "or" as used herein is to be interpreted as an inclusive or meaning any one or any combination. Therefore, "A, B or C" means any of the following: "A; B; C; A and B; A and C; B and C; A, B and C". An exception to this definition will occur only when a combination of elements, functions, steps or acts are in some way inherently mutually exclusive.

The drawings featured in the figures are for the purpose of illustrating certain convenient embodiments of the present invention, and are not to be considered as limitation thereto. Term "means" preceding a present participle of an operation indicates a desired function for which there is one or more embodiments, i.e., one or more methods, devices, or apparatuses for achieving the desired function and that one skilled in the art could select from these or their equivalent in view of the disclosure herein and use of the term "means" is not intended to be limiting.

The present invention relates to a process which includes a system and device for preventing the tangling of any electrical, optical, or fluid cords or tubes connected by a connector to a moving animal or cage during the medical testing of that animal. Data can be delivered to the animal or received from an animal. Also, manipulations of the animal can be done by any type of connectors. In one embodiment, the delivery or administration of data or experimental manipulations is accomplished by use of a multichannel microwire, multicarbon fiber, multisite silicon, ceramic electrode array, acoustic stimulation and recording, optical stimulation and recording, dialysis administration and sampling of fluids, or other sensors and actuators. These connections are controlled by a digital data system, such as a circuit board, a computer, a combination of the two, or any digital means to collect or administer data to or from an animal. The multichannel microwire electrode array or a multisite silicon or ceramic probes are embodiments of the invention used by inserting the array to individual neurons in the animal, or from different sites in the body, with an individual channel representing data to or from an individual neuron or individual location for sensing voltage. Connections to the animal for other uses could easily be made in view of this disclosure.

In other types of connections to the animal there would be a putative medical treatment, such as a tube connected to an animal for administration or sampling of a fluid containing molecules in solution or suspension, such as a drug, blood, plasma, or the like; or the withdrawal of an animal bodily fluid, such as brain or body interstitial fluid, blood, urine, or other liquid. The administration of a drug could be for use in testing the drug's efficacy, controlling the animal's behavior or physiological activity, affecting the neuronal data being collected, or the like. Bodily fluids could be received for the purpose of monitoring the animal during the testing of the animal by any means. Other animal connections could easily be determined and as long as the connections are tube or cord like in shape and nature, they would clearly work with the present invention. Other forms of animal connections might also work with the present invention and one faced with a different animal connection could clearly tell if the present invention were appropriate or not, however, in general, flexible connection like cords and tubes would be the most common type of connection. Wireless or optical connections with the animal are also to be used in the present invention, however, one would still utilize the position of a digital data system on or near the platform.

As used herein "test animals" are animals such as mammals; such as, rats, mice, and humans; birds; reptiles; any other living being, or the like, which have a tendency to move about in their cage in a manner that tangles any connection to the animal. Any animal that tolerates a tethered connection can be used. The same principle could be applied to a human animal in a space when use of a tethered system is appropriate and mobility is desired. The animal tethered connections allow for transfer of test data, fluid or optical connections, or any cable, tube, or the like connected to the animal during the testing of an animal in a test situation. The animals are normally in their own individual chambers. The chambers can be used to examine a wide range of neurophysiological or body behaviors when devices for sensory stimulation, feeding, drinking, and a means for behavioral observation are provided.

Chambers of the present invention could be nothing more than a bottom surface and sides (such as a box) with a top being optional if the sides are tall enough. In one embodiment, the chamber could be a room. Any material, such as metal, plastic, wood, or the like can be used. In one embodiment, the chamber is a Plexiglas type material so that the animal can easily be viewed without bars or the like obscuring the view of the animal. The chamber can include just the connections to the animal where the system sits mostly (from the turning unit, for example) above the chamber or can include sides high enough to include the entire system inside the chamber. One purpose of the chamber is to limit the movement area of the animal. Another purpose is to make devices accessible for interaction with the animal. A lever or photocell to detect movement or rotation of head position, a spout to drink fluid, and a trough or other device to obtain food are useful devices for inclusion in the animal chamber. Accordingly, for the purposes of this invention, "chamber" shall also refer to any means or device which limits the travel area (a fence or room, for example) of the animal during use of the system. In one embodiment, the rotating system is on the ceiling and allows the animal to roam within a large region, such as a room.

A "platform", as used herein, refers to a relatively flat, i.e., horizontal shelf of any desired shape (e.g. circular) for positioning elements of the system over the animal which benefits from being rotated to prevent twisting of the connection to the animal wherein the other end of the connection resides on the platform. The platform, for example, could have one or more liquid containers designed for delivering drugs or therapeutic modalities, one or more containers for collecting liquids from the animal, one or more computers, circuit boards for partial control of the system or tests being conducted (for example, to control release of a drug on a prescribed regimen), a device for collecting data from a multichannel microwire electrode array, timers, or any other chemical sensors, fluidic or optical device. The size and shape (overall dimensions) of the platform would be based on the desired device or object placed on the platform, the weight of objects on the platform, and the exact position of the platform over the animal. The platform could be square, round, polygonal, or the like as desired and as thick or thin for the particular use and user. Other considerations for size include if the platform is in the chamber that has limited dimensions or above the chamber, thus, allowing for dimensions larger than the floor or horizontal dimensions of the chamber below it. The platform employs a bearing to support its weight and is rotatable by any convenient means, such as by a center post or rod that is rotated or by a motor directly turning the platform itself. In one embodiment, the platform has a vertical center post hanging from above attached to a bearing to support weight, and is rotated by attaching a motor to the center post and using a motor to spin the center post. This could be done, for example, by attaching a motor to a belt drive and using the belt and pulleys to spin the center post. Power is transferred to the rotating system by using a multiple contact commutator system integrated into the post. Alternately, power could be transferred using coils and induction methods to transfer between stationary and rotating components.

The platform, as mentioned above, could be positioned above the chamber or within the chamber as desired. However, the closer to the animal, the shorter the connection will be between the animal and anything on the rotating platform. The platform could also have one or more holes for passing the animal connections through from the top of the platform to the animal underneath the platform. While the connections could be run over the edge of the platform holes near the center of the platform minimizing the distance, the connections need to run and provide less tendency to kink and twist during use of the present invention.

As used herein a "motor" for rotating the rotating platform refers to an NC or D/C motor with or without gears and pulleys which can rotate the platform in both a clockwise and counterclockwise direction. The rotation would be in small increments designed to be just enough rotation, such that as the animal turns in the cage, the platform rotates, thus preventing any connection to the animal from twisting or kinking. Accordingly, the motor must be able to engage and turn the platform incremental portions of a full rotation or more as needed. Control of this process is further explained below. The motor can be attached to a central post which is capable of turning the rotatable platform much in the manner that old phonograph turntables work with a drive belt attached to the drive shaft at the top or bottom and the like. But any method of turning the turntable would be acceptable and one skilled in the art could devise any number of motors, belts, and gears that could turn the rotatable platform. Likewise, while the particular embodiment depicted in the figures shows the motor at the top of the device, the motor could be located at any place convenient above or below the platform as designed given that there are a large number of ways to rotate things with motors. Again, one viewing the present invention would be able to figure other ways without undue experimentation.

"One or more sensors" refers to a means for detecting the animal movement, i.e. that the animal is turning in the cage and the ability to send that information to the motor in such a way that the motor could interpret the movement and determine which way to rotate and by how much as necessary. Sensors include photocells which could be triggered by movement, IR detection, radar, global positioning, video analysis with tracking, and the like. In one embodiment, the sensor comprises a rod and slot detection system. A rod and slot system of detection attaches a rod directly or indirectly to a cable from the animal, one end of the rod is then positioned in a slot (rectangular square oval, even circular, or the like). As the animal moves and causes twisting or movement of the cable, so does the rod within the slot. When the animal moves (for example, starts to rotate within the chamber) enough that the rod touches an edge of the slot, the position of touching is detected by electrical connection, magnetic switch, by breaking light path to a photocell, switch, or other like connection, thus creating an indication of where the animal is or in which direction and by how much the animal is rotating. Then a computer or other circuit, such as on the digital data system, can determine where the animal is and how much, if at all, the platform should be rotated to correct for animal movement. The rod hitting the left side or blocking light on the left photocell, for example, might indicate the need for counter-clockwise rotation while hitting the right side would indicate a reverse direction is needed. Detection of torsion of the cable through change in resistance of an element or change in magnetic field could achieve the same result. The exact location in the slot would indicate how much rotation is necessary, although a fixed amount could always be moved and then the system could reevaluate the animal position, and thus make a number of corrections as time passes. Photocells to detect the position of the rod are one other method. In general, if slot and rod, photocell, or any other detection system is used, the rotating right and left based on positioning of the animal is achieved by maintaining a digital feedback system which can be on the digital data system or separate which constantly records and evaluates the animal position. One skilled in the art, in view of the present disclosure could easily and without undue experimentation program a computer or the like to rotate the platform clockwise or counterclockwise in view of an animal position. The rod and slot detection system is an embodiment though that is simple and merely detecting where in the slot, the rod has to hit and activate a switch or block light to a photocell, and is a simple way of making such a determination. The relation of the rotations of the animal connection and the animal itself may change from animal to animal and connection type to connection type. No one particular system nor computation would suffice, but again, those changes in the program rotation amount can easily be built into the system, such that human or computer feedback can make corrections to the system that begins to over or under correct for rotation of the animal versus the platform.

As used herein the "hanging side S suspension support" refers to one method of supporting the cables or tubes making animal connections to help keep small animal movements from creating kinks, folds, twists, and bends when the platform fails to rotate with the animal movements, and thus reducing the need to rotate the platform manually to unravel twists. A tall chamber allows use of a larger area since simple rotation of the cable around the axis in the center at the top can be detected by alternate means. A cable with some stiffness is less prone to twist since its rotation is readily detected at a distance.

Counterweighting the end of the cable at the animal allows the animal to lift a lighter weight when moving, and removes the slack that allows twisting. The "hanging side S suspension" can be seen in FIG. 3 described later. The "hanging side S suspension" represents an instance of a class of physical arrangements of cable from the animal to the top of the chamber that is counter weighted to allow free movement of the animal and minimizes the formation of twists that effectively shorten the free cable. The "hanging side S suspension" allows use of a shorter height from the animal to the top of the chamber. The side S takes a portion of the cable or tube and suspends it from above, and in one embodiment to the bottom of the platform or otherwise, such that the connection also gets rotated during use of the system. The connections can be suspended by cable, thread, cord, or the like, however, any relatively thin suspension device like polymeric thread of sufficient diameter would be one embodiment. In this embodiment a nylon thread, such as fishing line, hangs from above the thin rod and is threaded through a hole in the rod which is offset from the axis of rotation. It is attached to a loop in the cable so that small movements of the animals will move the rod to block light to the photocell. As can be seen, the portion of the cable raised up is tied at the apex of that portion. The side S suspension also takes weight off of the cable and animal by providing an effective counter weight, and thus allows the animal to have a heavier connection than would otherwise be usable without the side S suspension system. The hanging S configuration can be achieved by use of an arm with weight opposite the cable to provide off set and effectively lighten the descending cable. Installing the movement sensors directly above the animal minimizes the tendency to kink and twist the cable when the animal rotates. Stainless steel springs protect the cable from damage, and use of multi-threaded silver coated copper wire reduces electrical noise. Other configurations with other connection support could also be used as necessary to provide support to the animal connections. It might also be noted that where multiple connections to the animal are used, for example, a multichannel array and a fluid drug connection, that the cables and tubes can be connected as if one cable, thus eliminating the need for multiple suspension systems or the possibility of the multiple connections getting tangled. In the case of a human animal, the Hanging-S class of connection could take the form of a hanging pole and platform with devices, an equivalent to a platform on rotating wheels of coasters that can be made to rotate with a human when moving within a space.

As used herein "digital data system" is an embodiment of a computer or other like device for collecting data differentially from the animal. In one embodiment the digital data system has a digital storage device positioned on the turn table. It can also refer to a data transfer method with external controls. A set of rings with contacts provide power for all elements of the rotation system. Data transfer can include transfer by wideband wireless, USB, or ultra wideband wireless, optical communication, wired connection optionally utilizing a multiple contact commutator system (including power transfer system). The system can be used for a number of processes in the present system to serve multiple channels for sensors and stimulation. The digital data system can collect and interpret data received from the animal, it can accurately time random events, and control the time of stimulation and release of drugs and other procedures used in the system. For example, when there is a liquid drug solution syringe pump positioned on the platform, it can control the time and amount of drugs depending on schedules and conditions. A second example is to control the patterns and timing of electrical or optical stimulation events. Computations for the rotation of the platform and the like can be done by the digital system. The digital data system can be a small circuit designed to perform limited activity, for example, rotation, data collection and drug delivery or can be a field programmable gate array, digital signal processor, computer, a mini-super computer with operating system and components, a quantum computer, and combinations of these components or any computational machine. By choosing a large external computer to receive data and send commands, multiple systems with multiple animals could be utilized with just a single computer to control other devices, archive data and analyze data. At least, a portion of the digital data system could be positioned on the platform if such is small enough. However, where a larger computer is necessary, for example, when acquiring and storing date on multichannel microwire electrode array type connections, chemical sensors, optical and fluidic devices, it might be necessary to position portions of the entire system of the invention separate from the present invention platform. In such cases where separate portions are necessary, a connector between the two is necessary as is a means of accurately synchronizing digital time clocks on or off the platform and possibly leaving a portion on the platform between the two devices. Multiple computers or digital devices for chemical sensing, microfluidics control, imaging via ultrasound, fluid flow determination, and other functions could also comprise the digital data system. Miniaturization of components allows many functions to be achieved. In that case, since the connection to the animal must rotate, and yet still be connected to the computer, use of a component of a slip ring connection can be used to provide time synchronizing event information and data transfer. Data transfer can be achieve using a combination of wireless network connections and wired connection using links of the commutator system. Such a connection is simple to use when a central vertical rod is used, and in one embodiment, it is placed at or near the top of the rod wherein connections can be strung down the rod through the platform and to the animal. Slip rings with different designs can be used to transfer data but are fairly expensive per channel, however, and one utilizing the system where possible would minimize the use of slip rings to power transfer and essential control functions. Slip rings with a central hole in the center rod can also be used when a portion of the rotating platform supports the fluid reservoir and pump system above the slip rings.

In order to utilize the present system in a method to develop therapy by testing the effectiveness of a therapeutic drug or an experimental procedure in an animal positioned in an animal chamber, there are a number of steps utilized which could not effectively be accomplished prior to the present invention. Once an animal is placed in the chamber of the system, the animal is connected to a drug delivery container with a means of dosing or stimulating the animal with a specific dose or stimulation pattern and a device to control the timing of such procedures. (General procedures of all types apply here—electrical or optical stimulation, behavioral training, etc.) Once the animal is connected to the drug delivery tubes of the system, the computer doses the animal or samples fluids at the predetermined intervals. The platform rotates clockwise and counterclockwise to prevent the tube of drug from kinking, and thus preventing dosages not reaching the animal when there is no attendant to watch the animal. Where there is a multichannel microwire electrode array, silicon or ceramic based array, other electrical or optical types of connections attached to the animal, the animal can be dosed and the effect on the animal measured. For example, a drug affecting neuronal processing could be administered and then the multichannel microwire electrode array (or other recording sensors and single or multi site probes systems) measure changes in the neuronal output, record it on a computer (digital data system), correlate with behavior and body physiology, and analyze the data. Because drug testing (and other procedures requiring measurement) usually happens over long times, at time days, weeks, or months, and because normally an animal would rotate and move so much during that time, the connections would be impossible to keep during an entire test without constant observation. The present invention provides a means of testing animals over long times, not before possible.

The system arrangement has the advantage of enabling multiple capabilities by using combinations of configurations for many different purposes. One embodiment deals with applications requiring electrical stimulation to activate brain or muscles by using electrodes optimized for high current flow. This is often achieved through use of platinum iridium wires or with surfaces coated with activated iridium oxide to maximized current flow for a given applied voltage. Multiple electrical connections are required to apply voltage to alternate stimulation sites. The rotating electronics system allows many sites to be selected and stimulated without need or limitation of multiple connections through rotating of commutator connections.

Another embodiment will employ one or more disposable or rechargeable batteries to power devices that rotate with the system to provide power for the computer and other circuits. Power will be provided to wireless devices to transmit data to external computers.

One embodiment of the invention enables analysis of multiple fluid samples to be acquired through use of micro dialysis probes. In this technique a small diameter u-shaped tubes made of a semipermeable membrane is inserted into brain or body tissue. Fluids are pumped slowly into the sampling u-shaped micro dialysis tubes using stepper motor systems to advance one or more fluid containing syringes. Drugs inside the tube may diffuse through the membrane into brain or body tissues to expose the tissue to a form of treatment or test. Alternately molecules of interest can diffuse from the tissue through the membrane into the lumen of the tube. Fluid may be collected by the distal end of the tube that extends above the animal to the rotating platform. Fluid exiting the tube can be collected for later analysis by instrumentation specialized for certain measurements. Alternately, the computer system with other circuits that rotates in parallel with movements of the animal in the chamber may control appropriate devices and sensors in order to perform tests in real time for presence and amount of molecules.

One embodiment uses a micro dialysis membrane to extract fluid containing dissolved ethanol from the body to follow the amount consumed and metabolized. Chemical tests then will determine presence and amount of ethanol in fluid exiting the return tube. Current generated by oxidation and reduction at an electrode will measure ethanol concentration directly. Alternately, a decrease in oxygen concentration in the fluid can be detected by an electrochemical sensor when the enzyme, alcohol dehydrogenase with ethanol and nicotinamide adenine dinucleaotide and ethnao as reagents, results in a product detected by colorimetric methods. Colorimetric tests based on other enzymes and substrates can be used. The use of computer instrumentation of small size on the rotating platform enables multiple dialysis fluid tubes to be employed and without need of a fluid swivel and with the advantage of a shorter length of tubing from the subject to the instrumentation for analysis.

Another embodiment uses antibodies that are specific for molecules of interest to be bound onto micro beads or nanoparticles suspended within the fluid flowing inside the micro dialysis tube. This arrangement captures specific molecules that diffuse from brain or body through the membrane to the suspended nanoparticles. Light is used to illuminate fluorescent molecules bound to the antibodies. Lenses and imaging sensors are used to image and measure optically the light intensity from the surface of the micro beads or nanoparticles. Images of the particles are scanned with software within the field programmable gate arrays and host computer to count particles and the intensity of emitted light to assess the presence and concentration of molecules of interest. In this way the presence and concentration of molecules within brain tissues are assessed to enable development of therapies. One or more of such systems can be combined with other devices rotated with the subject.

Another embodiment employs a large number of possible systems for chemical testing to be installed in the rotating system that would be made functional by the capability of controlling fluid flow using pumps, and with the ability to insert robes with arrays of specific chemical sensor site configured to detect different molecules. Chemical testing is made possible through the ability to perform electrochemical measurements of chemical reaction products, and with the use of light sources, optical sensors and imaging systems.

Further embodiments may employ one or more sensors including thermocouples, thermistors, strain gauges, proximity sensors, light emitting diodes to indicate position, acceleration rotation, and velocity, stretch, temperature, blood flow, detection, electrical activity of heart muscle and brain, and other parameters to determine body function. Sensors and actuators to create ultrasound images and ultrasonic sensors to detect fluid and blood flow will be used in the rotating configuration.

Another embodiment will use one or multiple light sources to activate optically active molecules and devices to stimulate biological processes. This configuration will be used to activate proteins that increase ion flow through neuronal membranes which then cause excitation or inhibition of neurons actions. This configuration would be useful to activate or release caged or bound compounds to release molecules with actions for investigating therapeutic effects of molecules and treatments.

Another embodiment will use one or more combinations of multiple light sources and light sensors, imagers, scanners, lenses, filter combinations, acoustic, and cameras to capture optical images from body parts or images of the surroundings of the subject. One or more microscopic images can be obtained of light or fluorescent images of tissues and cellular components.

Another embodiment will provide power to enable actuator and sensor components for one or more ultrasonic imaging units to capture images of body components in behaving animals either alone or in combination with other sensors or stimulation units.

Multiple simultaneous observations can be made possible of brain, heart and tissue activity.

Now referring to the drawings for one embodiment of the present invention. FIG. 1 is a relationship chart of the elements of an embodiment of the present invention. This figure depicts an embodiment with an animal having both a multichannel microwire electrode array connection, an optical, and a fluid drug connection. In FIG. 1, animal chamber 1 contains animal 2. Animal 2 has sensors, microwire or probe implant, electrical recording, stimulation or electrochemical sensor sites, or optical 3, and fluid connections 4 to or from the animal 2. The multiple sensor or implant could be neuronal or other types of connections as noted in the general description.

Movement and rotation of the animal is detected by a sensor which causes rotation of the system connected to the animal 2. One instance of the rotation sensor consists of a rod or tab 5a and device with slot 5b. Movement of the rod 5a in either direction blocks one of two photocells which activates movement of the rotating system in a direction to follow the movement of the animal. The rod can be placed near the top of a tall hanging version of the cable system, or moved by a swinging movement of a wire positioned to hold up the cabling system. Signals from the rod 5a and slot position detector 5 are sent to motor activation circuits or the PC control board 15 via wire 14 which then sends a signal to the motor via wire 14a. In other embodiments, the sensor may be a video tracker or is directly connected to the motor. The slot and rod device is described in more detail in FIG. 3.

Positioned above the animal chamber 1 is rotating platform 10. Sitting on rotating platform 10 is liquid source 11 which supplies fluid to the animal 2 via. In this embodiment the multichannel microwire electrode or sensor array is connected via PC control board 15 along connecting wires 16. The PC control board 15 is connected to a PC 17 for collection of data via slip ring 18. The PC control board 15 and PC together constitute the digital data system. A motor 19 is positioned to rotate the platform 10 clockwise and counterclockwise. The slip ring 18 rotates with the platform 10 and keeps a connection of the PC control board 15 to the PC for collection of data. In other embodiments, there is no PC control board and all computer based connections are through the PC 17 and slip ring 18 connection down the wires 16 to animal 2. In other embodiments, there is no PC and only digital data system on the platform.

Figure 2A:
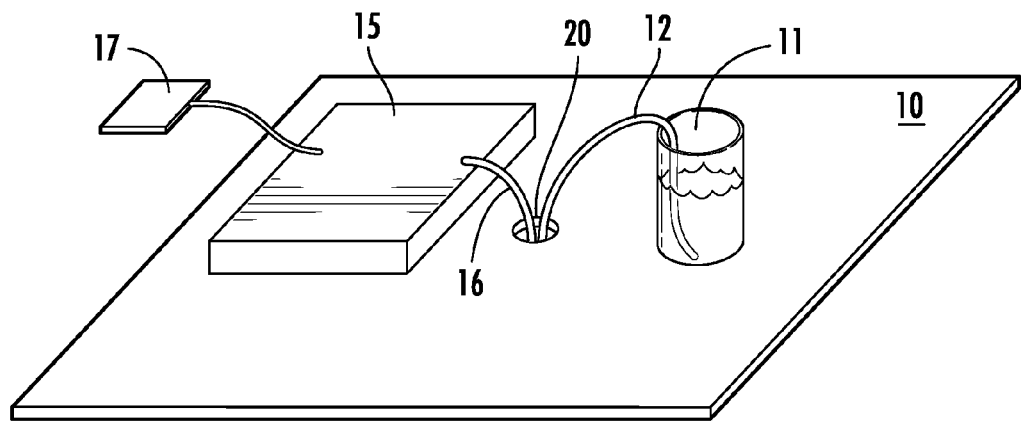
FIGS. 2a and 2b depict embodiments of the platform and means for rotating the platform.
Figure 2B:
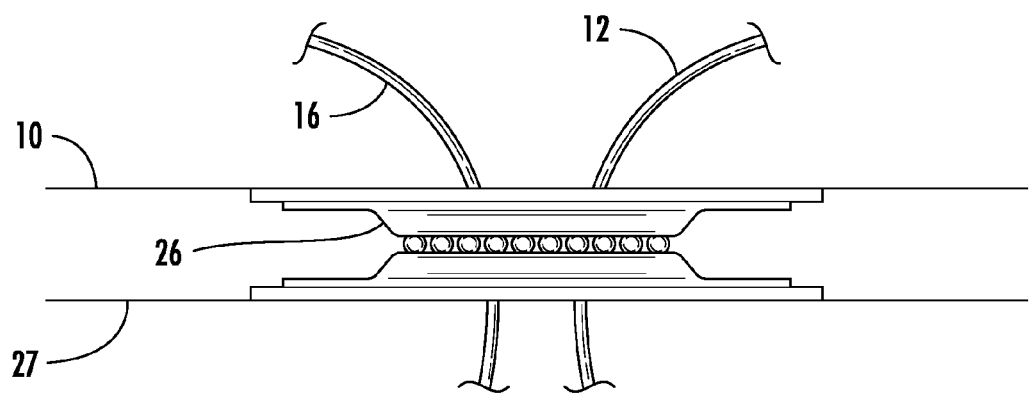
Figure 2C:
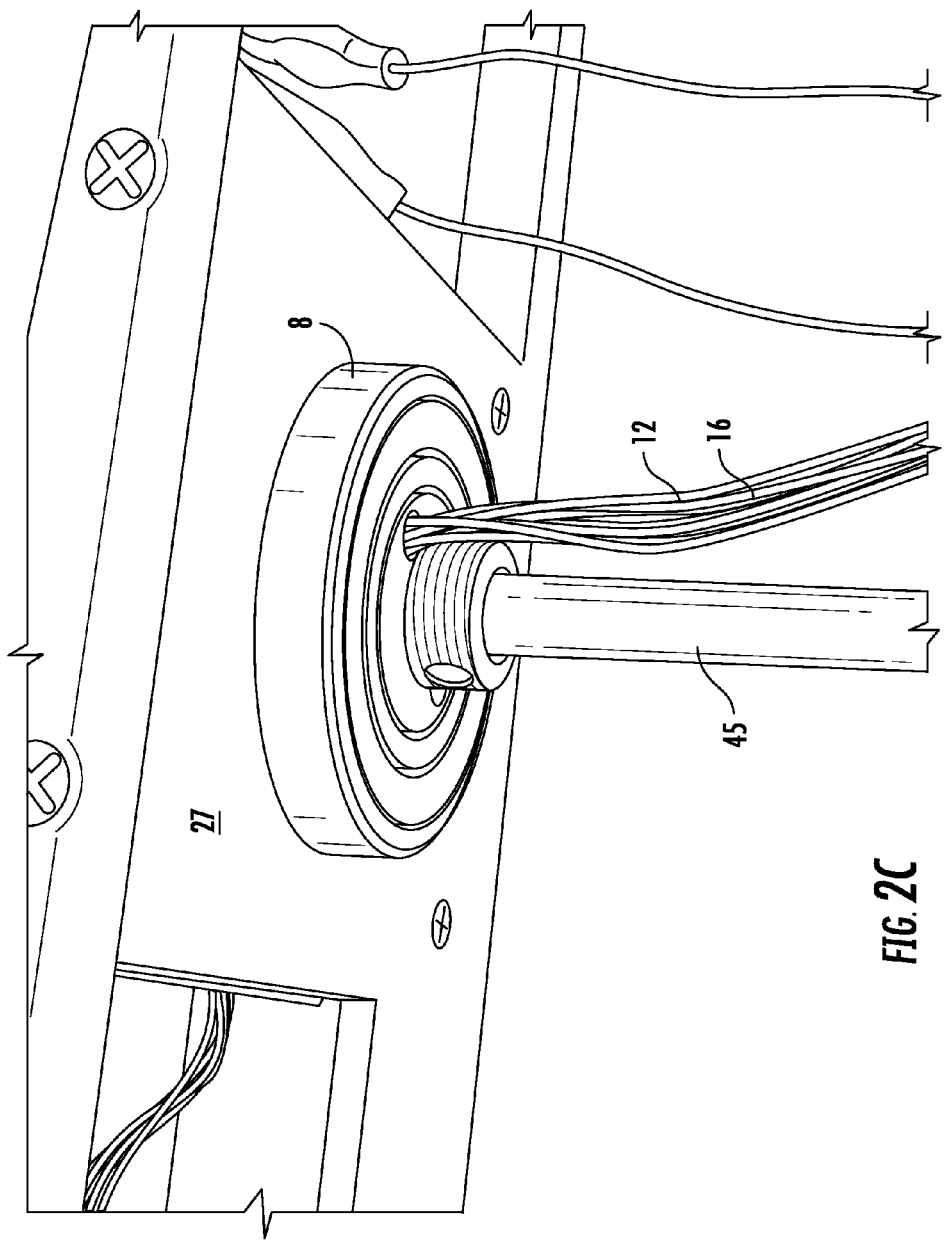

FIGS. 2a, 2b, and 2c depict embodiments of the rotating platform wherein there is hole 20 in roughly the center of the platform 10. The liquid tube 12 and control board wiring 16 are fed through hole 20 and down to the animal as shown in other figures. Other tethered connections can be utilized in this manner. In the side view of 2b, the tubing and wiring can be seen passing through the platform 10. A ball bearing turntable 26 has platform 10 sitting on it while the turntable 26 rests in this embodiment on roof of chamber 27. The turntable 26 in this position also allows support to the platform and everything on the platform 10 such that less effort is needed to turn the platform 10 by the motor and more items can be placed on platform 10. In FIG. 2c another alternative method of rotating where a support disc is shown supporting a platform and is bolted to shaft 45, and the shaft supports one or more platforms from above.

Figure 3:
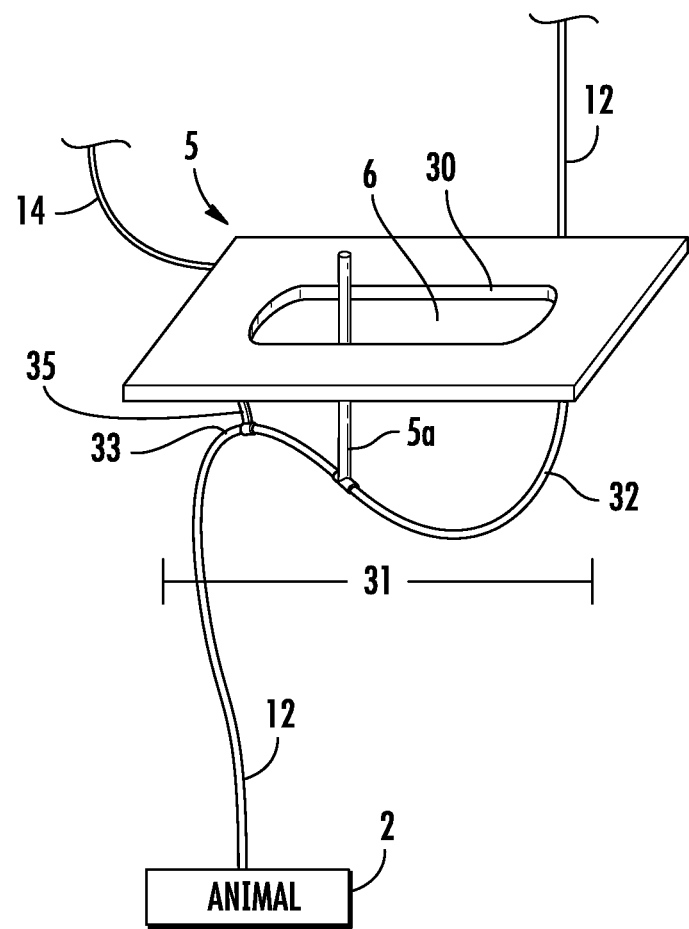
FIG. 3 is a perspective view of a rod and slot movement sensor.

FIG. 3 shows a side view of the rod and slot position sensor of the invention as well as an embodiment of the side S hanging connection support. Fluid connection tube 12 is shown in S configuration 31 having vally 32 and mountain 33 portions of the hanging connection 31. A hanging thread 35 connects tube 12 at the mountain point 33 up and hangs from the bottom of the rod and slot device 5. Movement of the animal moves the S shaped cable, which moves the hanging thread, which moves the rod to break the path between the light source and photocell, which activate circuits that cause movement of the motor that rotates the platform. In this case, the sensor will rotate with the platform 10. In other embodiments, the thread could attach directly to the platform 10. It is understood that the connection should be such that it rotates in sync with the platform as described above.

Figure 4:
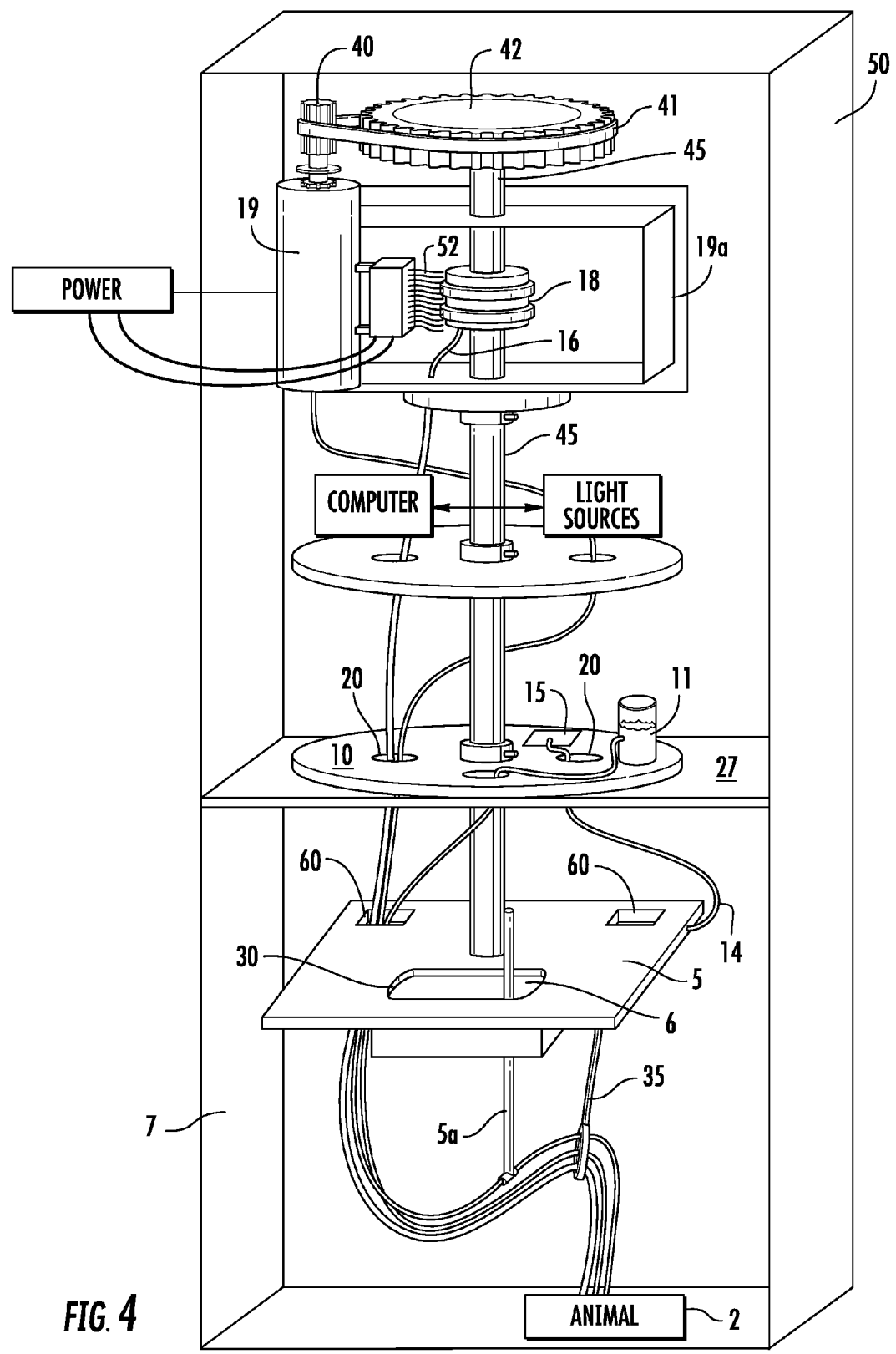
FIG. 4 is a perspective view of an embodiment of the present invention.

FIG. 4 depicts a more detailed embodiment of the present invention. In this embodiment, motor 19 attached to motor support 19a drives gear 40 in both a clockwise and counterclockwise manner. In one embodiment, the motor support 19a could be attached to chamber top wall 50. In other embodiments, the motor 19 is fixedly attached to a wall or other stationary item. A belt 41 is connected to the motor gear 40 and to a pulley on the vertical rod gear 42. Vertical rod gear 42 is connected to vertical rod 45. The rotation of gear 40 in a clockwise or counterclockwise direction causes vertical rod gear 42 to spin in the same manner. Thus, the spinning of vertical rod gear 42 causes the vertical rod 45 to spin in tandem with the vertical rod gear 42. The rotation clockwise or counterclockwise of the vertical rod 45 causes everything attached to the rod 45 to rotate in tandem with the rod 45. A commutator 50 is shown.

In this embodiment, three items are attached to and rotate with the vertical rod 45. A slip ring 18 is affixed to the vertical rod 45. As the slip ring 18 rotates, brushes 52 make and maintain contact, thus allowing power to be transferred to all devices that rotate and data received from cable 16 to be transferred to the computer 17 via cable 17a. Platform 10 is located on chamber top 27 and is connected to vertical rod 45. Platform 10 also rests on turntable 26 (not seen in this view, but seen in FIG. 2b) which rests on chamber top 27, thus the platform 10 is supported by its connection to the rod 45 and it is resting on turntable 26. In this view, three holes 20 are shown. Instead of them being in the center of platform 10, they are shown a short distance from vertical rod 45. Cables 12 and 20 are shown threaded through holes 20. Lastly, at the bottom portion of rod 45, there is shown rod and slot detector 5 which is shown to also have holes 60 for further threading the cables. Note that the sensor 5 rotates with the animal and has the cable suspension 35 attached to a bottom portion much like in FIG. 3.

When animal 2 moves around, the cables move with the animal causing movement rod 5a to move within slot 6. When sides 30 are touched, by rod 5a then a signal is sent to motor 19 to rotate the vertical rod to compensate for the movement of the animal 2. The amount of movement is calculated by a digital feedback system on the PC control board 15, the PC 17, or any other device placed in the system for calculating the movement required to compensate for movement of animal 2. In this view, the chamber 1 is shown as clear Plexiglas, and while it has roof 27, the sides 50 and others stand up past the top of the entire system.

Clearly, other embodiments of the present invention are possible in light of the teaching and embodiments as well as the drawings herein. Those variations and limitation from embodiments are contemplated within the scope of the present invention and the claims which follow should be so interpreted.

Those skilled in the art to which the present invention pertains may make modifications resulting in other embodiments employing principles of the present invention without departing from its spirit or characteristics, particularly upon considering the foregoing teachings. Accordingly, the described embodiments are to be considered in all respects only as illustrative, and not restrictive, and the scope of the present invention is, therefore, indicated by the appended claims rather than by the foregoing description or drawings. Consequently, while the present invention has been described with reference to particular embodiments, modifications of structure, sequence, materials and the like apparent to those skilled in the art still fall within the scope of the invention as claimed by the applicant.

What is claimed is:

1. An animal test system for use with a moving tethered test animal comprising:
   a. an animal chamber having a bottom surface for containing the test animal;
   b. a rotating platform positioned above the animal chamber bottom;
   c. a motor for rotating the platform clockwise and counterclockwise;
   d. at least one connector for a tethered connection to the animal for delivering or receiving at least one of optical, electrical, or fluid connection to the animal wherein an opposite end of the connector is positioned on the platform;
   e. one or more movement sensors positioned to sense the movement of the animal in the chamber wherein the one or more sensors are used to send movement data to a digital feedback system which controls the motor to rotate the platform clockwise or counterclockwise based on the animal movement sensed in a manner to prevent unwanted twisting of the animal tethered connection;
   f. a digital data system in digital communication with the connection to the animal; and
   g. a connector support which takes at least a portion of the weight off the animal by holding the tethered connection in a fixed S shaped configuration.

2. The system according to claim 1 wherein a movement sensor comprises a rod and slot motion sensing system.

3. The system according to claim 1 wherein the animal connection comprises one or more liquid containers positioned on the platform connected to the animal.

4. The system according to claim 3 wherein a device for controlling the release of a liquid drug is positioned on the platform.

5. The system according to claim 1 wherein the animal connector comprises a multichannel microwire electrode array designed for acquiring or delivering at least one of neural signals from a plurality of single neurons, and a plurality of measurement signals to and from the animals.

6. The system according to claim 1 wherein the digital data system is positioned on the platform.

7. The system according to claim 1 wherein at least a portion of the digital data system is positioned separate from the animal.

8. The system according to claim 7 wherein portions of the digital data system is connected via a slip ring connection.

9. The system according claim 7 wherein there are synchronizing pulses to synchronize the portions.

10. The system according to claim 1 wherein a computer is positioned entirely on the platform.

11. The system according to claim 1 wherein the platform is rotated via a centrally positioned vertical rod and motor driven belt system.

12. The system according to claim 1 wherein at least one movement sensor is a photo cell type sensor.

13. A method for testing the effect of a drug in an animal positioned in an animal chamber comprising:
   a. positioning a motorized rotating platform above a floor of the chamber;
   b. placing a desired quantity of the drug in liquid form in a drug delivery container, positioning the container on the platform and creating a tethered connection of the drug container to the animal the tethered connection supported in a fixed S-shaped configuration;

c. positioning one or more movement sensors to sense the movement of the animal in the chamber which can control a motor to rotate the platform clockwise or counterclockwise based on the animal movement sensed in a manner to prevent unwanted twisting of the animal connection to the drug container;

d. delivering the drug to the animal; and e. monitoring the results of the administered drug while rotating the platform to account for the animal movement.

14. The method according to claim 13 comprising attaching at least one of a multichannel microwire electrode array, multiple sensors, optical sensor, electrical sensor, and stimulation contacts to the animal in the chamber designed for acquiring or delivering neural signals from a plurality of single neurons in the animal, all parts of the brain, all parts of the body in a manner that the rotating platform, and one or more sensors keeps the array or animal connections from undesired twisting.

15. The method according claim 13 further comprising a digital data system in digital communication with the animal.

16. The method according to claim 15 wherein at least a portion of the digital data system is positioned on the platform.

17. The method according to claim 16 wherein at least a portion of the digital data system on the platform is synchronized with any other portions of the digital data system not on the platform by a synchronizing pulse.

18. The method according to claim 13 which further comprises sampling fluids from the animal's brain or body in a desired manner.

19. A method for testing the effect of a procedure on an animal positioned in an animal chamber comprising:

a. positioning a motorized rotating platform above a floor of the chamber;

b. creating a tethered animal connection to the animal to monitor the animal the tether comprising a connector support which takes at least a portion of the weight off the animal by holding the tethered connection in a fixed S-shaped configuration;

c. positioning one or more movement sensors to sense the movement of the animal in the chamber which can control a motor to rotate the platform clockwise or counterclockwise based on the animal movement sensed in a manner to prevent unwanted twisting of the animal connection;

d. performing the procedure on the animal; and e. monitoring the results of the procedure while rotating the platform to account for the animal movement.

20. The method according to claim 19 comprising attaching at least one of a multichannel microwire electrode array, multiple sensors, optical sensor, electrical sensor, and stimulation contacts to the animal in the chamber designed for acquiring or delivering neural signals from a plurality of single neurons in the animal, all parts of the brain, all parts of the body in a manner that the rotating platform, and one or more sensors keeps the array or animal connections from undesired twisting.

21. The method according claim 19 further comprising a digital data system in digital communication with the animal.

22. The method according to claim 21 wherein at least a portion of the digital data system is positioned on the platform.

23. The method according to claim 22 wherein at least a portion of the digital data system is on the platform and synchronized with any other portion of the digital data system not on the platform by a synchronizing pulse.

24. The system according to claim 1, 13 or 19 with multiple two way connections consisting of the group of at least one of electrical, fluid, and optic connections with an animal.

25. The system according to claim 1, 13 or 19 wherein the animal is a human animal.

26. The system according to claim 1, 13 or 19 where there is a digital data system with at least a portion positioned on the platform.

27. An animal test system for use with a moving tethered test animal comprising:

a. an animal chamber having a bottom surface for containing the test animal;

b. a rotating platform positioned above the animal chamber bottom having an entire computer positioned on the platform in digital communication with the animal;

c. a motor for rotating the platform clockwise and counterclockwise connected to a power source which transfers power to the computer and the rest of the system using a multiple contact commutator;

d. at least one connector for a tethered connection to the animal for delivering or receiving at least one of optical, electrical, or fluid connection to the animal wherein an opposite end of the connector is positioned on the platform;

e. one or more movement sensors positioned to sense movement of the animal in the chamber wherein the one or more sensors are used to send movement data to a digital feedback system to the computer which controls the motor to rotate the platform clockwise or counterclockwise based on the animal movement sensed in a manner to prevent unwanted twisting of the animal tethered connection; and f. a connector support which takes at least a portion of the weight of the at least one connector off the animal.

28. The test system according to claim 27 wherein the platform is bearing supported.

* * * * *